United States Patent [19]

Gordon

[11] 4,203,993

[45] May 20, 1980

[54] 6α-BROMOPENICILLANIC ACID SULFONE

[75] Inventor: Eric M. Gordon, Pennington, N.J.

[73] Assignee: E. R. Squibb & Sons, Inc., Princeton, N.J.

[21] Appl. No.: 968,539

[22] Filed: Dec. 11, 1978

[51] Int. Cl.$^2$ .................... A61K 31/43; C07D 499/44
[52] U.S. Cl. ................ 424/271; 260/239.1; 260/245.2 R
[58] Field of Search .............. 260/306.7 C, 239.1; 424/270, 271

[56] References Cited

U.S. PATENT DOCUMENTS

| | | | |
|---|---|---|---|
| 3,197,466 | 7/1965 | Chow et al. | 260/239.1 |
| 3,741,959 | 6/1973 | Looker et al. | 260/239.1 |

FOREIGN PATENT DOCUMENTS 956605  4/1964  United Kingdom.

OTHER PUBLICATIONS

Fisher et al., Annual Reports in Medicinal Chem. 13,239 (1978).
Cole, Enzyme Biotechnology, p. 222 (1978).
Clayton, J. Chem. Soc. (C), 2123, (1969).
Loosemore et al., J. Org. Chem. 43, (18) 3611 (1978).
Pratt et al., Proc. Natl. Acad. Sci. USA, 75 (9) 4145, (1978).
English et al., Antimicrobial Agents & Chemotherapy, 14(3) 414 (1978).
Sykes et al., J. of Antimic Chemotherapy, 2,115 (1976).

*Primary Examiner*—Norman Morgenstern
*Assistant Examiner*—Vera C. Clarke
*Attorney, Agent, or Firm*—Lawrence S. Levinson; Dale Lovercheck; Donald J. Barrack

[57] ABSTRACT

(2S,5R,6S)-6α-Bromo-3,3-dimethyl-7-oxo-4-thia-1-azabicyclo[3.2.0]heptane-2-carboxylic acid, S,S-dioxide, physiologically acceptable salts thereof and readily hydrolyzable ester thereof inhibit the action of the β-lactamase enzyme RTEM.

6 Claims, No Drawings

6α-BROMOPENICILLANIC ACID SULFONE

BACKGROUND OF THE INVENTION

Bacteria that are normally susceptible to attack by β-lactam antibiotics can develop a resistance to such attack by the production of a β-lactamase enzyme. These enzymes catalyze the hydrolysis of the lactum ring of a β-lactam antibiotic to a β-amino acid derivative, which is not active against bacteria.

One β-lactamase enzyme is the RTEM enzyme. The RTEM enzyme is of plasmid origina and is said to be the most widely distributed β-lactamase among the enteric gram-negative bacteria; see, Fisher et al., *Annual Reports in Medicinal Chemistry*, 13:239 (1978). The RTEM enzyme is capable of transferring into bacteria that are susceptible to β-lactam antibiotics and rendering the organism resistant to these drugs; this ability to transfer from organism to organism, of course compounds the problem of the RTEM enzyme. This can be seen most clearly in the development recently of an ampicillin-resistant strain of *N. gonorrhoeae*.

Two approaches have been followed in the search for a way to overcome, or at least minimize, the effects of β-lactamases. The first is the synthesis of novel β-lactam antibiotics which are stable against β-lactamases. These efforts have enjoyed some success; however, the resistant derivatives synthesized seem to have a lower degree of antibacterial activity than the non-resistant analogs. The second approach comprises the use of a compound which inhibits the action of β-lactamase enzymes on the lactam ring of a β-lactam antibiotic. These β-lactamase inhibitors are used in conjunction with the β-lactam antibiotics.

RELATED APPLICATION

United States patent application Ser. No. 968,538, filed Dec. 11, 1978 discloses that (2S,5R,6S)-6β-bromo-3,3-dimethyl-7-oxo-4-thia-1-azabicyclo[3.2.0]heptane-2-carboxylic acid, S,S-dioxide, salts thereof, and readily hydrolyzable esters thereof, are inhibitors of the β-lactamase enzyme RTEM.

BRIEF DESCRIPTION OF THE INVENTION (2S,5R,6S)-6α-Bromo-3,3-dimethyl-7-oxo-4-thia-1-azabicyclo[3.2.0]heptane-2-carboxylic acid, S,S-dioxide, salts thereof, and readily hydrolyzable esters thereof, are inhibitors of the β-lactamase enzyme RTEM. This invention is directed to the above-named novel sulfone compound, to compositions comprising the above-named compound in combination with a β-lactam antibiotic susceptible to degradation by the RTEM enzyme, and to a method of inhibiting the action of the β-lactamase enzyme RTEM on a β-lactam antibiotic by the use of one of the above-named compounds.

DETAILED DESCRIPTION OF THE INVENTION

The novel compound of this invention, (2S,5R,6S)-6α-bromo-3,3-dimethyl-7-oxo-4-thia-1-azabicyclo[3.2.0]heptane-2-carboxylic acid, S,S-dioxide, is obtained by oxidizing the corresponding 6α-bromopenicillanic acid. The oxidation can be accomplished using any of the methods known to be useful for oxidizing a sulfur atom. Exemplary of the oxidizing agents which can be used are metachloroperbenzoic acid, hydrogen peroxide, sodium metaperiodate, etc. The oxidation reaction can be run in an organic solvent, e.g., ethyl acetate. Reaction temperature is not critical, and the reaction is conveniently run at room temperature.

6α-Bromopenicillanic acid is a known compound (see, for example, Cignarella et al., *J. Org. Chem.*, 27:2668 (1962)), and can be obtained by the diazotization of a 6-aminopenicillanic acid at 0–2° C. in dilute hydrobromic acid.

Physiologically acceptable salts of (2S,5R,6S)-6α-bromo-3,3-dimethyl-7-oxo-4-thia-1-azabicyclo[3.2.0]heptane-2-carboxylic acid, S,S-dioxide are readily obtained using conventional techniques and are useful as β-lactamase inhibitors. Exemplary of the salts specifically contemplated are those formed with a metal ion, e.g., alkali metal, ions or alkaline earth metal ions, or amine salt ions.

Readily hydrolyzable esters of (2S,5R,6S)-6α-bromo-3,3-dimethyl-7-oxo-4-thia-1-azabicyclo-[3.2.0]heptane-2-carboxylic acid, S,S-dioxide are easily obtained using conventional techniques and are useful as β-lactamase inhibitors. Exemplary of the ester groups which are readily hydrolyzed in vivo are those having the structural formula —CH(Y)—O—CO—alkyl, wherein Y is hydrogen or alkyl, e.g., acetoxymethyl and pivaloyloxymethyl; methoxymethyl; and isobenzofuranyl.

As discussed above, under the heading "Background of the Invention", the RTEM enzyme is a β-lactamase enzyme that catalyzes the hydrolysis of the lactam ring of a β-lactam antibiotic yielding a derivative which is not active against bacteria. The treatment of a mammalian host with a β-lactam antibiotic susceptible to degradation by the RTEM enzyme can be made more effective by the administration of (2S,5R,6S)-6α-bromo-3,3-dimethyl-7-oxo-4-thia-1-azabicyclo[3.2.0]heptane-2-carboxylic acid, S,S-dioxide, or a physiologically acceptable salt thereof, or a readily hydrolyzable ester thereof, in conjunction with the antibiotic. A compound of this invention can be administered simultaneously with a β-lactum antibiotic or separately.

Compositions comprising an RTEM enzyme inhibitor of this invention and a β-lactam antibiotic susceptible to degradation by the RTEM enzyme are within the scope of this invention. The weight ratio of inhibitor to antibiotic can be from about 1:10 to 10:1, preferably from about 1:3 to 3:1. Formulation of these compositions can be accomplished using conventional techniques, e.g., in powder or for reconstitution with a sterile vehicle for injection in solution; in suspension for oral administration; or the like. The compositions will preferably be formulated for administration in the manner conventionally used for administration of the antibiotic.

Many of the known β-lactam antibiotics have been shown to be susceptible to degradation by the RTEM enzyme. Current thinking (see, for example, Sykes et al., *J. of Antimic. Chemotherapy*, 2, 115 (1976) is that most of the penicillin antibiotics are susceptible (although to varying degrees) to degradation by the RTEM enzyme. Exemplary penicillins are ampicillin, amoxicillin, penicillin V, penicillin G, carbenicillin, and sulbenicillin. The cephalosporins are not as susceptible as the penicillins to degradation by the RTEM enzyme; cephaloridine and cephalothin are exemplary of cephalosporins that are susceptible to degradation by the RTEM enzyme.

The following example is illustrative of this invention.

EXAMPLE (2S,5R,6S)-6α-Bromo-3,3-dimethyl-7-oxo-4-thia-1-azabicyclo[3.2.0]-heptane-2-carboxylic acid, S,S-dioxide.

To a cold (0–5° C.) solution of m-chloroperbenzoic acid (20.00 g) in ethyl acetate (200 ml) is added (2S,5R,6S)-6-bromo-3,3-dimethyl-7-oxo-4-thia-1-azabicyclo[3.2.0]heptane-2-carboxylic acid (5.6 g, 20 mM) in ethyl acetate (30 ml). After stirring overnight at 26° C., the reaction mixture is diluted with ethyl acetate (300 ml) and extracted with saturated sodium bicarbonate solution (2×150 ml). The combined aqueous extracts are acidified to pH 2 with concentrated hydrochloric acid and extracted quickly with ethyl acetate (3×200 ml). The combined organic extracts are dried over sodium sulfate and concentrated under reduced pressure and elevated temperature to afford a white solid. This material is a mixture of the desired product and m-chlorobenzoic acid. Trituration (3×) with hexane (1 liter), yields a white solid (5.7 g) free of almost all m-chlorobenzoic acid.

An analytical sample is prepared as follows. Approximately 1 g of product is dissolved in chloroform/hexane and brought to the cloud point. After one hour, the filtrate is decanted from oil which has deposited on the flask. Upon standing for about 16 hours the filtrate gives crystals, which are recrystallized from hot benzene to yield the title compound, melting point 139°–140° C.; IR (KBr) 1793, 1780 (sh), 1755 cm$^{-1}$; NMR (acetone-d$_6$) 1.50 (s, 3H), 1.60 (s, 3H), 4.48 (s, 1H), 5.16 (d, 1H, J=2 Hz), 5.40 (d, 1H, J=2 Hz).

Anal. Calc'd. for C$_8$H$_{10}$BrNO$_5$S: C, 30.78; H, 3.23; N, 4.48; S, 10.27; Br, 25.60.

Found C, 30.98; H, 3.11, N, 4.62; S, 10.32; Br, 25.52.

What is claimed is:

1. (2S,5R,6S) -6α-Bromo-3,3-dimethyl-7-oxo-4-thia-1-azabicyclo[3.2.0]heptane-2-carboxylic acid, S,S-dioxide, or a physiologically acceptable salt thereof or a readily hydrolyzable ester thereof.

2. A compound in accordance with claim 1, (2S,5R,6S)-6α-bromo-3,3-dimethyl-7-oxo-4-thia-1-azabicyclo[3.2.0]heptane-2-carboxylic acid, S,S-dioxide.

3. A method of inhibiting the action of the β-lactamase enzyme RTEM in a mammalian host being treated with a β-lactam antibiotic susceptible to degradation by the RTEM enzyme, which comprises administering (2S,5R,6S)-6α-bromo-3,3-dimethyl-7-oxo-4-thia-1-azabicyclo[3.2.0]heptane-2-carboxylic acid, S,S-dioxide, or a physiologically acceptable salt thereof or a readily hydrolyzable ester thereof to the host in conjunction with the antibiotic.

4. A method in accordance with claim 3 wherein the compounds is (2S,5R,6S)-6α-bromo-3,3-dimethyl-7-oxo 4-thia-1-azabicyclo[3.2.0]heptane-2-carboxylic acid, S,S-dioxide.

5. A composition comprising a β-lactam antibiotic susceptible to degradation by the β-lactamase enzyme RTEM and (2S,5R,6S)-6α-bromo-3,3-dmethyl-7-oxo-4-thia-1-azabicyclo[3.2.0]heptane-2-carboxylic acid, S,S-dioxide, or a physiologically acceptable salt thereof or a readily hydrolyzable ester thereof.

6. A composition in accordance with claim 5 comprising a β-lactam antibiotic susceptible to degradation by the β-lactamase enzyme and (2S,5R,6S)-6α-bromo-3,3-dimethyl-7-oxo-4-thia-1-azabicyclo[3.2.0]-heptane-2-carboxylic acid, S,S-dioxide.

* * * * *

UNITED STATES PATENT AND TRADEMARK OFFICE
CERTIFICATE OF CORRECTION

PATENT NO. : 4,203,993

DATED : May 20, 1980

INVENTOR(S) : Eric M. Gordon

It is certified that error appears in the above–identified patent and that said Letters Patent are hereby corrected as shown below:

Column 1, line 12, change "origina" to -- origin --.

Signed and Sealed this

Twenty-ninth Day of July 1980

[SEAL]

*Attest:*

SIDNEY A. DIAMOND

*Attesting Officer*  *Commissioner of Patents and Trademarks*

Notice of Adverse Decision in Interference

In Interference No. 100,886, involving Patent No. 4,203,993, E. M. Gordon, 6α-BROMOPENICILLANIC ACID SULFONE, final judgment adverse to the patentee was rendered Mar. 4, 1983, as to claims 1 and 2.

[*Official Gazette June 14, 1983.*]